United States Patent [19]

Kitamura

[11] Patent Number: 4,677,247
[45] Date of Patent: Jun. 30, 1987

[54] PROCESS FOR PRODUCING NEW VARIETY OF ODORLESS SOYBEANS

[75] Inventor: Keisuke Kitamura, Morioka, Japan

[73] Assignee: Taishi Foods Company Ltd., Aomori, Japan

[21] Appl. No.: 769,235

[22] Filed: Aug. 26, 1985

[30] Foreign Application Priority Data

Aug. 27, 1984 [JP] Japan .................................. 59-176732

[51] Int. Cl.$^4$ ................................................ A01H 1/02
[52] U.S. Cl. .......................................... 800/1; 47/58; 47/DIG. 1
[58] Field of Search .................. 47/58, DIG. 1; 800/1

[56] References Cited

U.S. PATENT DOCUMENTS

| | | | |
|---|---|---|---|
| 3,903,645 | 9/1975 | Bradner | 47/58 |
| 4,077,157 | 3/1978 | Bradner | 47/58 |
| 4,545,146 | 10/1985 | Davis | 47/58 X |

*Primary Examiner*—Robert E. Bagwill
*Attorney, Agent, or Firm*—Armstrong, Nikaido, Marmelstein & Kubovcik

[57] ABSTRACT

A new variety of odorless soybean and a process for producing the new variety. The new soybean is characterized by breeding to produce a variety which holds the recessive $lx_2$ and $lx_3$ genes. These genes dominate the lipoxygenase L-2 and L-3 lacking characteristic.

2 Claims, No Drawings

PROCESS FOR PRODUCING NEW VARIETY OF ODORLESS SOYBEANS

DETAILED DESCRIPTION OF THE INVENTION

The present invention relates to a process for producing a new variety of odorless soybean which are free from the grassy flavor which is peculiar to soybeans.

BACKGROUND OF THE INVENTION

A soybean seed contains therein a large quantity of the enzyme lipoxyenase which accelerates oxidation of unsaturated fatty acids such as linolic and linolenic acids, which are components of soybean oil.

The action of the enzyme is so intensive that when the dry seed is crushed, and under conditions where the enzyme, soybean oil and oxygen (in air) are mixed and contacted with each other, oxidation occurs. The produced, oxidized substance (hydroperoxide), is further decomposed to produce an aldehyde or alcohol. These products have an undesirable taste characterized by a grassy flavor and bitterness, thus posing a significant problem in the production of soybean oil and soybean protein foods.

The normal soybean seed has, three kinds of lipoxigenase, L-1, L-2 and L-3. Their physical and chemical properties are as follows:

·L-1:

(a) L-1 has an optimum pH which is around pH9, and it has a low activity for any substrate with a pH which is around neutral.

(b) The L-1 enzyme acts well on free fatty acids such as linolic acid, but it does not act well on neutral fats such as triglyceride.

(c) L-1 is relatively heat stable as compared to L-2 and L-3.

L-2:

(a) L-2 has an optimum pH which is around pH7.

(b) The L-2 enzyme has a much higher activity for arachidonic acid as compared to L-1 and L-3. It acts well on neutral fats such as triglyceride.

L-3:

(a) L-3 is similar to L-2. It has an optimum pH which is around pH7.

(b) The L-3 enzyme, relatively, acts well on free fatty acids such as linolic acid and neutral fats such as linolic acid ester or triglyceride.

PRIOR ART

In order to decrease the oxidization of soybean oil and the occurrence of an undesirable flavor caused by lipoxigenase, inactivation of lipoxigenase has mainly been carried out by heating. Further, attempts have been made to remove the undesirable flavor by using processes such as cooking, extraction by organic solvents or decomposition by the enzyme, aldehyde dehydrogenase. However, these extreme processes result in a loss of function of the soybean protein as a food material, and the mild processes sometimes result in an incomplete deodorizing effect.

DESCRIPTION OF THE INVENTION

The present inventor has made various studies relating to processes for producing odorless soybeans, free from the disadvantages encountered in prior art in connection with soybean deodorizing processes noted above. As a result the inventor has found that the above-described object may be achieved in an extremely effective manner by means of a soybean breeding procedure. Based upon this, the inventor has accomplished the present invention.

(1) Selection of crossing parent

It is generally known that lipoxygenases L-1, L-2 and L-3 are involved in producing the grassy flavor and bitterness of soybeans. However, it has not been known which enzyme had been most involved in the occurrence of the grassy flavor.

The present inventor has found, as a result of a foretaste of uncooked soybeans lacking L-1, L-2 and L-3, respectively, that the grassy flavor in soybeans lacking L-1 is not reduce much. However, soybeans lacking in L-2 or L-3 have a considerably lower grassy flavor. The inventor found that if soybeans could be produced with the L-2 and L-3 enzyme eliminated at the same time, the occurence of the grassy flavor would be almost entirely suppressed.

The present inventor has selected, out of known soybean varieties, a crossing parent which comprises P.I. 86023 for the soybean genotype lacking in L-2 and Wasenatsu Ichigowase, Tohoku No. 74 as the soybean lacking in L-3, Saikai No. 20 and the other two cultivars which are known for the soybean genotype lacking in L-3. The P.I. 86023 is available from the U.S. Department of Agriculture, North Laboratory, and the soybean lacking in L-3 such as Wasenatsu is available from the Japanese Ministry of Agriculture, Forestry & Fisheries, Tohoku Agricultural Experimental Station, subject to a formal procedure.

(2) Analysis of the dominant gene lacking in L-2 of P.I. 86023 and of the dominant gene lacking in L-3 of Wasenatsu:

Prior to crossing the P.I. 86023 and the Wasenatsu as the example of a soybean lacking in L-3, the analysis of the dominant genes lacking in lipoxygenase was conducted.

It has been confirmed that as a result of the analysis of the segregation ratio regarding the characteristic lacking in L-2 of the $F_2$ seed and the $F_3$ seed of Suzuyutaka x P.I. 86023, the characteristic lacking in L-2 of P.I. 86023 is controlled by a single recessive gene $lx_2$, and as the result of the analysis of the segregation ratio regarding the characteristic lacking in L-3 of the $F_2$ seed of Raiden x Wasenatsu and Century x Wasenatsu, the characteristic lacking in L-3 of Wasenatsu is controlled by a single recessive gene $lx_3$.

(3) One example of a breeding process (see Table 1)

Crossing was made using Wasenatsu as the genotype lacking in L-3, obtained from Japanese Ministry of Agriculture, Forestry & Fisheries Tohoku Agricultural Experiment Station (Kariwano) on the mother's side and P.I. 86023 as the genotype lacking in L-2 obtained from the U.S. Department of Agriculture, North Laboratory on the father's side to obtain $F_1$ seeds. The $F_1$ plants were subjected to selfing to obtain $F_2$ seeds, and 10 to 20 mg of cotyledon cut-pieces, from opposite the hypocotyl of each seed were analyzed to select two seeds lacking in L-2 and L-3 enzymes. The thus selected two $F_2$ plants were subjected to selfing to obtain $F_3$ seeds. From these plants 50 yellow coat seeds were selected, and 10 to 20 mg of cotyledon cut-pieces were analyzed to confirm the lacking in L-2 and L-3 enzyme characteristic. After this, $F_3$ plants were grown. When the plants were grown, five individuals which had many adherent seeds per individual were selected. The $F_4$ seeds were again subjected to systematic cultivation. Thereafter, selection was repeated in accordance with a conventional process (a systematic breeding process) to obtain an $F_8$ seeds in August 1984. This completed the breeding of a new variety A.

TABLE 1

Breeding Process of New Variety A

| Year | Generation | Breeding Place |
|---|---|---|
| Nov. 1982 | Wasenatsu (lacking $L_3$) × P.I. 86023 (lacking $L_2$) | Iwate Univ. hothous (pot cultivation) |
| Jan. 1983 | $F_1$ | Iwate Univ. hothous (pot cultivation) |
| Apr. 1983 | $F_2$ (two seeds lacking $L_2$, $L_3$) | Iwate Univ. hothous (pot cultivation) |
| Jul. 1983 | $F_3$ (Selection of yellow coat seeds lacking in $L_2$, $L_3$) Selection of good plants | Iwate Univ. hothous (pot cultivation) |
| Sept. 1983 | $F_4$ (All lacking in $L_2$, $L_3$, the same below) Selection of good individuals | Iwate Univ. hothous (pot cultivation) |
| Dec. 1983 | $F_5$ | Iwate Univ. hothous (pot cultivation) |
| Mar. 1984 | $F_6$ Systematic cultivation of selected individuals Confirmation of fixation degree Systematic cultivation of selected individuals Confirmation of fixation degree | Iwate Univ. hothous (pot cultivation) Iwate Univ. hothous (pot cultivation) |
| June 1984 | $F_7$ Systematic cultivation of selected individuals Final systematic selection | Iwate Univ. field |
| Aug. 1984 | $F_8$ New variety A Multiplication | |

(4) The main properties of the crossing parents and new variety A, other than the characteristic of lacking in lipoxygenase, are as shown in Table 2.

TABLE 2

| Characteristic Variety | Flower color | Hair color | Seed color | Umbilical color | Cotyledon color | Shape | Growing property | Early or late | Remarks |
|---|---|---|---|---|---|---|---|---|---|
| Wasenatsu | white | brown | yellow | light-brown | yellow | circular | limited | Extreme premature | Summer soybean in the Kyushu district, small size |
| P.I. 86023 | purple | " | green | black | " | circular | " | Premature | Slightly flatten in shape |
| New variety A | " | " | yellow | light-brown | " | circular | " | Premature | Slightly larger in size than Wasenatsu |

(5) Results of sensory evaluation tests regarding the flavor-suppressing effects of new variety A Ten subjects ate uncooked soybeans of the normal variety, Raiden, having L-1, L-2 and L-3, soybeans P.I. 408251 lacking in L-1, soybeans P.I. 86023 lacking in L-2, soybeans Wasenatsu lacking in L-3 and soybeans of new variety A lacking in both L-2 and L-3. Sensory evaluation tests were conducted and the results of the tests are as shown in Tables 3 and 4:

TABLE 3

| Variety | Grassy Flavor |
|---|---|
| Raiden | + + + |
| P.I. 408251 | + + |
| P.I. 86023 | + |
| Wasenatsu | + + |
| New breed A | − |

+ + + All people intensively tasted a grassy flavor
+ + All people tasted a grassy flavor
+ Most people slightly tasted a grassy flavor
− All people did not taste a grassy flavor

TABLE 4

| Grassy flavor Variety | Extreme taste | Intensive taste | Considerable taste | Slight taste | No Taste at all |
|---|---|---|---|---|---|
| Raiden | 9 (person) | 1 | 0 | 0 | 0 |
| P.I. 408251 | 0 | 5 | 5 | 0 | 0 |
| P.I. 86023 | 0 | 0 | 2 | 7 | 1 |
| Wasenatsu | 0 | 3 | 5 | 2 | 0 |
| New variety A | 0 | 0 | 0 | 0 | 10 |

Note: Table 4 indicates the number of persons showing the degree of grassy flavor of the soybean varieties.

As is apparent from the results of the sensory evaluation test shown in Tables 3 and 4, the new variety A is excellent in odor-suppressing effect. The new variety has less undesirable taste than any of the normal varieties and the soybeans lacking in L-1, L-2 and L-3, respectively. New variety A is substantially odorless.

(6) Results of electrophoresis of new variety A

The concentration of a buffer solution for preparation in a Davis system electrophoresis method was set at $\frac{1}{3}$ of a normal method, and 7M urea was added to prepare a polyacrylamide gel. Two ml of 0.5M tris-hydrochloric acid buffer solution (pH 8.0) containing 8M urea and 0.1M 2-mercaptoethanol per 10 to 20 mg of soybean pieces was added to seeds of P.I. 408251, Norin No. 2, Tohoku No. 74, Raiden, P.I. 86023, Wasenatsu and five seeds of new variety A, to make samples.

20 to 30 l of sample was applied and electrophoresis was conducted at a constant voltage of 200 V.

$A_5$ and $A_6$ are $A_5$ and $A_6$ subunits of soybean glycinin protein, respectively. $Ti^1$, $Ti^2$ and $Ti^3$ are $Ti^1$ type, $Ti^2$ type and $Ti^3$, respectively, of the soybean Kunitz trypsin inhibitor protein.

Table 5 summarises the absence and presence of both $A_5$ and $A_6$ subunits and the $Ti^1$, $Ti^2$ and $Ti^3$ types of Kunitz trypsin inhibitor.

TABLE 5

| | Presence and absence of both $A_5$ and $A_6$ subunits | Type of Kunitz trypsin inhibitor |
|---|---|---|
| P.I. 408251 | Presence | $Ti^2$ |
| Norin No. 2 | Absence | $Ti^2$ |
| Tohoku No. 74 | Absence | $Ti^2$ |

TABLE 5-continued

| | Presence and absence of both $A_5$ and $A_6$ subunits | Type of Kunitz trypsin inhibitor |
|---|---|---|
| Raiden | Absence | $Ti^3$ |
| P.I. 86023 | Presence | $Ti^2$ |
| Wasenatsu | Presence | $Ti^1$ |
| New variety A | Presence | $Ti^2$ |

For cultivation of the new variety A, conventional cultivation methods for normal soybean varieties may be used.

(7) Method for selection of soybean lacking in L-2 and L-3 in the present invention The presence and absence of L-2 and L-3 may be confirmed by shaving off, with a safety razor, 10 to 20 mg of cotyledon from opposite the hypocotyl of a seed and to analyze it in the following methods. The remaining seed including the hypocotyl may be germinated and grown, if necessary.

(a) Since the L-1, L-2 and L-3 may be separated by the SDS-polyacrylamide gel electrophoresis as developed and improved by the present invention, the presence and absence of L-2 and L-3 may be confirmed.

(b) Anti L-2 serum is prepared using a rabbit, and the presence and absence of L-1, L-2 and L-3 may be confirmed by the immune double diffusion method of Octalony.

(c) Since L-1, L-2 and L-3 may be separated by DEAE-Sephacel column chromatography, activities thereof may be measured to thereby confirm the presence of L-2 and L-3.

The above-described method is not suitable for selection of individual seeds since more than 500 mg of soybean powder are required.

The (b) and (c) methods were used for confirmation, as necessary, after selection has been made by the method (a).

More specifically, in the method (a), the SDS concentration of electrode buffer solution in the Laemmli's method is changed from 0.1% to 0.125%. The electrophoresis is carried out on 7% gel at 150 V for a long period of time (7 to 8 hours) to separate L-1, L-2 and L-3 proteins.

SUMMARY OF THE INVENTION (1) In the prior art, in order to remove the grassy flavor of soybeans, physical and chemical deodorizing treatments have been carried out with attendant drawbacks. On the other hand, deodorizing treatment is made unnecessary by the breading of a new variety of odorless soybean.

(2) A crossing parent was selected on the basis of new knowledge that in the breeding of a new variety, the occurrence of grassy flavor is almost entirely suppressed by the breeding of soybeans lacking in both L-2 and L-3, of the lipoxigenases L-1, L-2 and L-3 involved in the oxidation of soybean oil and the production of grassy flavor.

(3) The soybean variety lacking in both L-2 and L-3 was made possible by selecting and breeding as the soybean lacking in L-2, the soybean variety P.I. 86023 having a single recessive gene $lx_2$ which dominates the L-2 lacking characteristic and as the variety lacking L-3, the soybean variety Wasenatsu having a single recessive gene $lx_3$ which dominates the L-3 lacking characteristic.

(4) Soybean variety A obtained by the present invention is almost totally free from grassy flavor, a property that is difficult to be expected from the odor-suppressing effect of the parents.

What is claimed is:

1. A process for producing a new variety of odorless soybean, comprising crossing a soybean genotype having a single recessive gene $lx_3$ which dominates a lipoxygenase L-3 lacking characteristic with a soybean geneotype P.I. 86023 having a single recessive gene $lx_2$ which dominates a lipoxygenase L-2 lacking characteristic, to produce a variety holding genes $lx_2$ and $lx_3$ in common, lacking in lipoxygenases L-2 and L-3, and thereby breeding a new variety A of odorless soybean free from grassy flavor which is peculiar to soybeans, and multiplying the new variety.

2. A new variety of odorless soybean free from grassy flavor which is peculiar to soybeans, holding recessive gene $lx_2$ which dominates a lipoxygenase L-2 lacking characteristic and recessive gene $lx_3$ which dominates a lipoxygenase L-3 lacking characteristic.

* * * * *